United States Patent
Hwang

Patent Number: 5,725,597
Date of Patent: Mar. 10, 1998

[54] ARTIFICIAL HIP-JOINT

[76] Inventor: Sung Kwan Hwang, Ra-dong 604, Saja Apt., San 71, Koyo 2-dong, Songpa-ku, Seoul 138-112, Rep. of Korea

[21] Appl. No.: 747,098

[22] Filed: Nov. 8, 1996

[30] Foreign Application Priority Data

Nov. 9, 1995 [KR] Rep. of Korea ................ 95 40456

[51] Int. Cl.$^6$ ............................................. A61F 2/28
[52] U.S. Cl. ........................... 623/23; 623/18; 606/67
[58] Field of Search ............................. 623/18, 19, 23; 606/65, 66, 67, 68

[56] References Cited

U.S. PATENT DOCUMENTS

| | | | |
|---|---|---|---|
| 2,612,159 | 9/1952 | Collison | 606/67 |
| 4,129,903 | 12/1978 | Huggler | 606/67 |
| 5,376,125 | 12/1994 | Volnkler | 623/23 |
| 5,389,107 | 2/1995 | Nassar et al. | 623/23 |

FOREIGN PATENT DOCUMENTS

| | | | |
|---|---|---|---|
| 3538346 | 5/1987 | Germany | 623/23 |
| 8603962 | 7/1986 | WIPO | 623/23 |

OTHER PUBLICATIONS

A.H. Crenshaw; pp. 442–473, vol. 1–8, Campbell's Operative Orthopaedics.

*Primary Examiner*—David Isabella

[57] ABSTRACT

An artificial hip-joint having a construction capable of reducing abrasion of a polyethylene layer formed within the acetabulum cup when the head of the femur pivots in the acetabulum cup. The artificial acetabulum cup is implanted in the acetabulum of a user's pelvic bone and includes a hollow hemispherical member made of a metal. The polyethylene layer is formed on the inner surface of the hemispherical member. A femur head holder is fixed to the femur. The femur head holder includes a spherical metal femur head pivotally held in the artificial acetabulum cup, a shaft coupled at an upper end thereof to the femur head and adapted to support the femur head, a housing extending inclinedly through the greater trochanter of the femur and adapted to receive the shaft therein in such a manner that it rotates with respect to the shaft, and bearings mounted between the shaft and the housing and adapted to support axial and radial load applied to the shaft at the femur head by the weight of the user. The bearings allows the housing to rotate with respect to the shaft when the user performs a movement involving a rotation of the femur head in the acetabulum cup, so that the movement of the user can be conducted while preventing the rotation of the femur head in the acetabulum cup.

10 Claims, 6 Drawing Sheets

ARTIFICIAL HIP-JOINT

BACKGROUND OF THE INVENTION

1. Field of the Invention

The present invention relates to an artificial joint, and more particularly to an artificial hip-joint having a construction capable of dispersing or distributing the shear force applied to the surface of the artificial joint to avoid a local over-abrasion phenomenon occurring at the acetabulum cup due to a concentration of stress, thereby achieving an extension in life of the hip-joint.

2. Description of the Prior Art

The hip-joint of human body is the joint consisting of the upper end of the femur of each leg supporting the body on the ground, namely, the head of the femur, and the acetabulum cup of the pelvic bone coupled to the head of the femur.

The upper part of the body is connected to legs by two hip-joints, respectively. For this reason, serious trouble in walking and exercising may occur when any one of such hip-joints is damaged.

The damage of the hip-joint may be primarily generated when the head of the femur is damaged due to a vascular necrosis. Secondarily, the hip-joint may be damaged when the neck of the femur fractures due to a traffic accident or falling accident. In either case, the damaged hip-joint should be replaced by an artificial hip-joint.

Examples of conventional artificial hip-joints are illustrated in FIGS. 1A and 1B, respectively.

Referring to FIG. 1A, an artificial hip-joint is shown which includes a hollow hemispherical acetabulum cup 2 implanted in the acetabulum of the pelvic bone 1. A shaft 4 extends inclinedly through the greater trochanter 3' of the femur 3 while protruding outwardly at its opposite ends. The hip-joint also includes a spherical femur head 5 fixed to the upper end of the shaft 4 and pivotally fitted in the acetabulum cup 2, a support member 6 coupled to the lower end of the shaft 4 and adapted to firmly support the shaft 4 on the femur 3, and a clamping member 7 adapted to clamp the support member 6 to the lower end of the shaft 4. The femur head 5 is integral with the shaft 4.

FIG. 1B shows another conventional artificial hip-joint in which its shaft 4' adapted to support the femur head 5 is constituted by a stem. The shaft 4' is inserted into a space formed in the central portion of the femur 3 after removing the marrow existing in that portion of the femur.

In either case, the acetabulum cup 2 has a double structure consisting of a hollow hemispherical member 8 made of a titanium alloy and a polyethylene layer 9 formed on the inner surface of the hemispherical member 8. A porous coating are bonded to the outer surface of the hemispherical member 8. After the implantation, the acetabulum cup 2 can be more firmly coupled to the pelvic bone 1 by virtue of the porous coating as the pelvic bone 1 is grown. The polyethylene layer 9 formed on the inner surface of the hemispherical member 8 contains the femur head 5 made of a metal such as a cobalt chromium alloy in such a manner that the femur head 5 pivots smoothly. When the user walks, the femur head 5 rotates and moves in X-Y axis directions within the acetabulum cup 2. During such movements, the femur head 5 generates face friction with the polyethylene layer 9 of the acetabulum cup 2, thereby resulting in abrasion of the polyethylene layer 9. As a result, fine polyethylene particles are generated.

Such fine polyethylene particles generated during the pivotal movement of the metal femur head 5 on the polyethylene layer of the acetabulum cup 2 are problematic in that they generate osteolysis at the part of pelvic bone 1 around the artificial hip-joint. It is known that the reason why polyethylene particles having a grain size of, in particular, 1 to 5 μ, generate osteolysis is because IL-1 and TNF are released while the polyethylene is eaten by macrophages, thereby resulting in an inflammatory reaction.

The abrasion of the polyethylene layer results in a reduction in the life of the artificial hip-joint. Moreover, the artificial hip-joint may be dislocated due to side effects caused by fine polyethylene particles generated upon the abrasion of the polyethylene layer. Such a dislocation of the artificial hip-joint causes the user to feel pain. Furthermore, there is an increase in hospital expense.

SUMMARY OF THE INVENTION

Therefore, an object of the invention is to provide an artificial hip-joint having a construction capable of preventing occurrence of osteolysis after the implantation of the artificial hip-joint while reducing abrasion generated between the head of the femur and the polyethylene layer formed within the acetabulum cup, thereby increasing the durability of the artificial hip-joint.

In accordance with the present invention, this object is accomplished through an artificial hip-joint comprising an artificial acetabulum cup implanted in the acetabulum of a user's pelvic bone, the artificial acetabulum cup consisting of a hollow hemispherical member made of a metal and a polyethylene layer formed on the inner surface of the hemispherical member, and a femur head holder fixed to a femur, the femur head holder comprising a spherical metal femur head pivotally held in the artificial acetabulum cup, wherein the femur head holder further comprises: a shaft coupled at an upper end thereof to the femur head and adapted to support the femur head; a housing extending inclinedly through the greater trochanter of the femur and adapted to receive the shaft therein in such a manner that it rotates with respect to the shaft; and bearing means mounted between the shaft and the housing and adapted to support axial and radial load applied to the shaft at the femur head by the weight of the user, the bearing means allowing the housing to rotate with respect to the shaft when the user performs a movement involving a rotation of the femur head in the acetabulum cup, so that the movement of the user can be conducted while preventing the rotation of the femur head in the acetabulum cup.

The bearing means comprises a taper roller bearing fitting around a middle portion of the shaft, and at least one needle bearing fitting around a lower portion of the shaft.

The housing has a larger-diameter portion provided at an upper portion thereof and adapted to receive the taper roller bearing, and cover means fixedly mounted to the upper end of the larger-diameter portion and adapted to seal the interior of the housing, thereby preventing metal grains formed during the rotation of the shaft from leaking from the interior of the housing.

The cover means comprises a typical cover. Preferably, the cover means comprises a magnetic fluid seal member.

The magnetic fluid seal member includes a magnet, a magnetic fluid, and O-rings so as to prevent fine metal grains formed in the housing during the rotation of the shaft from leaking outwardly from the interior of the housing. In other words, fine metal grains, which may leak through gaps defined between the outer surface of the shaft and the inner surface of the magnetic fluid seal member and between the inner surface of the housing and the outer surface of the magnetic fluid seal member, are attracted by the magnetic force of the magnet. Accordingly, it is possible to prevent fine metal grains from leaking outwardly from the interior of the housing.

BRIEF DESCRIPTION OF THE DRAWINGS

Other objects and aspects of the invention will become apparent from the following description of embodiments with reference to the accompanying drawings in which.

DETAILED DESCRIPTION OF THE PREFERRED EMBODIMENTS

Figure 1A:
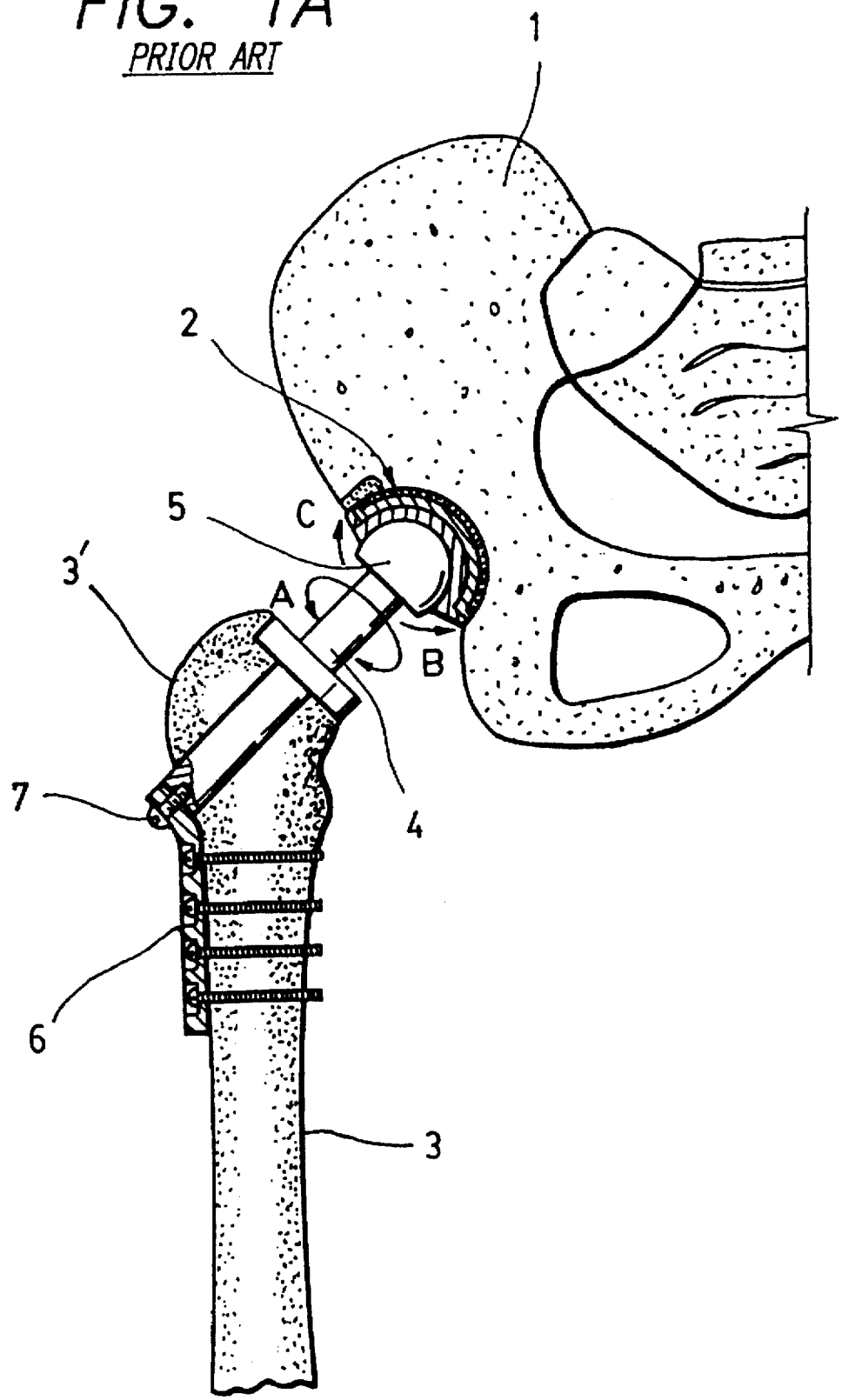
FIGS. 1A and 1B are sectional views respectively illustrating conventional artificial hip-joints.
Figure 1B:
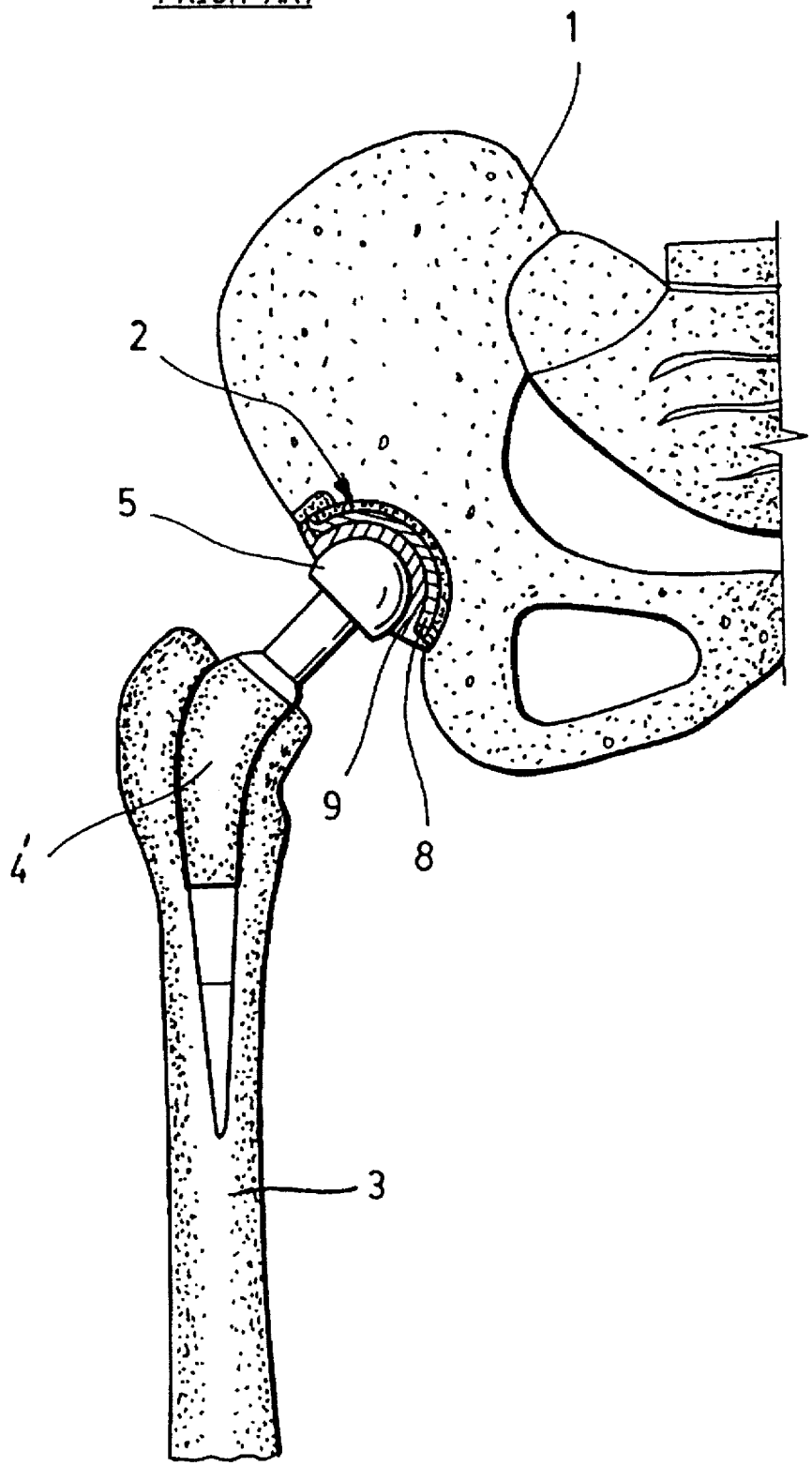
Figure 2:
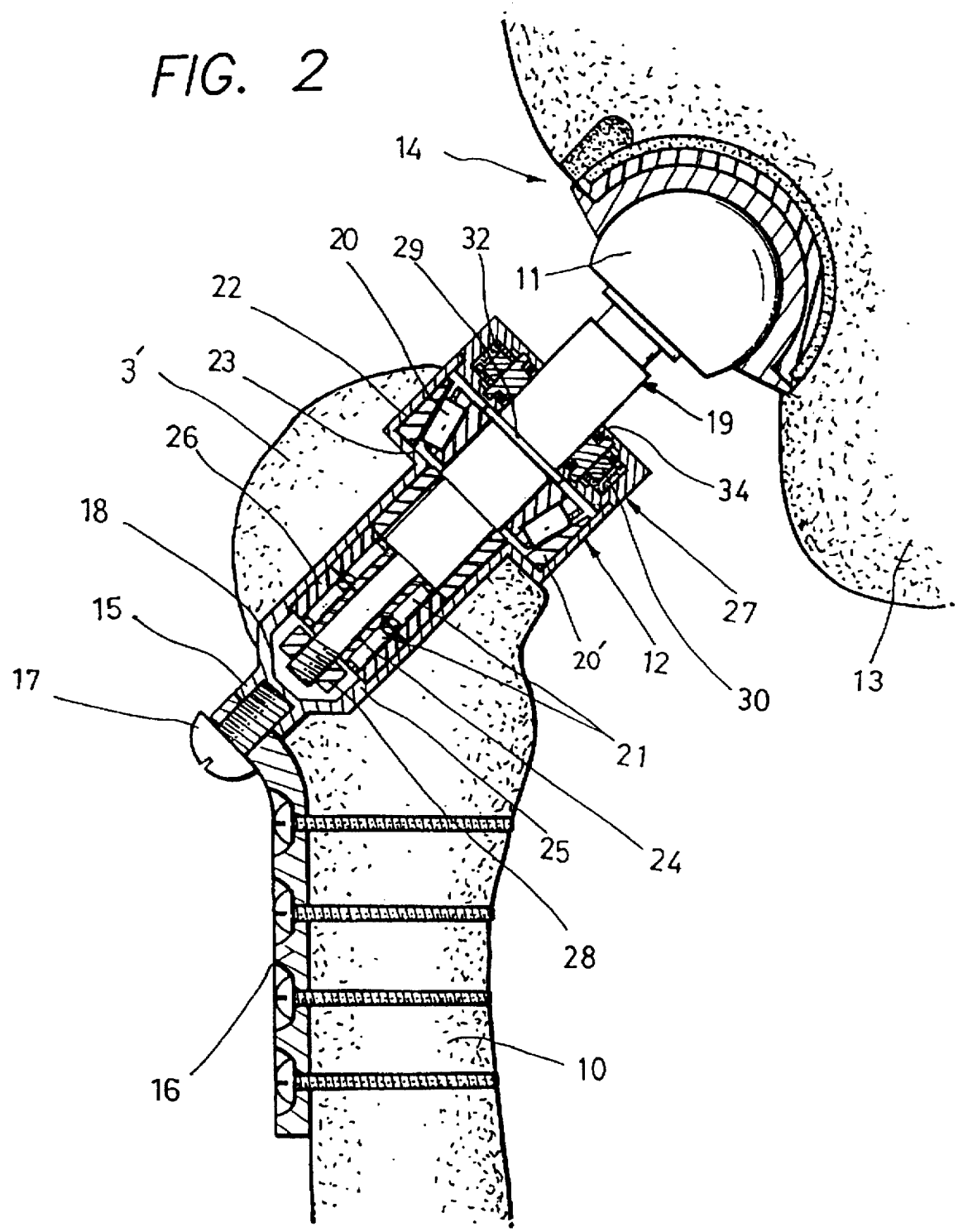
FIG. 2 is a sectional view illustrating an artificial hip-joint according to an embodiment of the present invention.
Figure 3:
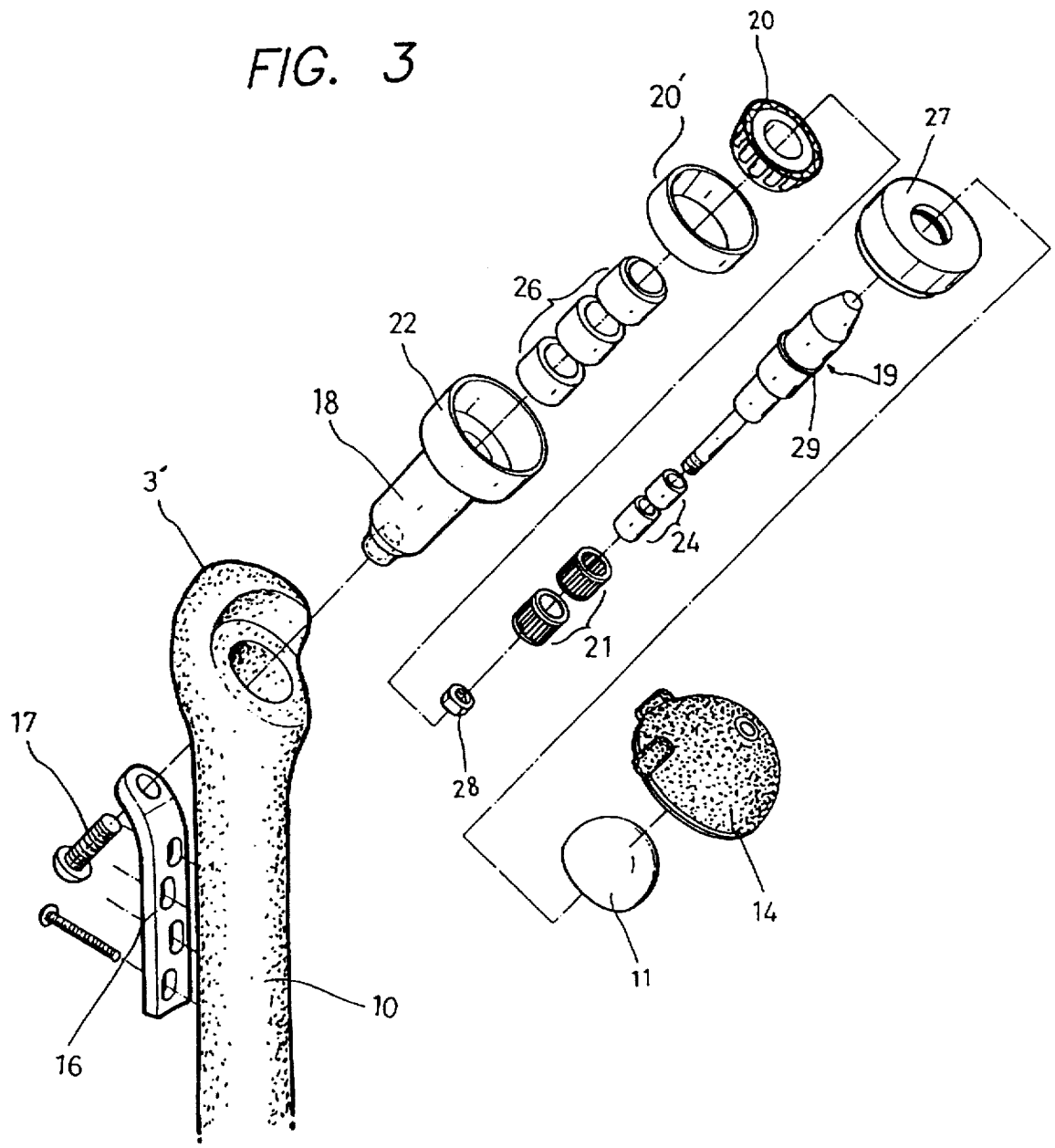
FIG. 3 is an exploded perspective view illustrating the artificial hip-joint of FIG. 2.

FIGS. 2 and 3 illustrate an artificial hip-joint according to an embodiment of the present invention.

As shown in FIGS. 2 and 3, the artificial hip-joint of the present invention includes a metal femur head 11 mounted to the upper end of the femur 10, a femur head holder 12 adapted to support the metal femur head 11 on the upper end of the femur 10, and an artificial acetabulum cup 14 implanted in the acetabulum of the pelvic bone 13 and adapted to contain the metal femur head 11 in such a manner that the metal femur head 11 pivots freely. The femur head 11 has a spherical shape.

The femur head holder 12 extends inclinedly through the greater trochanter 3' of the femur 10 while protruding outwardly at its opposite ends. Preferably, the inclination of the femur head holder 12 is 135°. The lower end 15 of the femur head holder 12 protrudes outwardly through the outer cortical bone of the femur 10. A support member 16 having a well-known construction is firmly coupled to the lower end 15 of the femur head holder 12 by a fixing means 17. The support member 16 is fixed to the femur 10. The support member 16 serves to withstand the femur head holder 12 on the femur 10 against the component of load applied in the longitudinal direction of the femur head holder 12 due to the weight of the user exerted on the metal femur head 11.

In accordance with the present invention, the femur head holder 12 includes a housing 18 extending inclinedly through the upper end of the femur 10. The housing 18 is fixed to the upper end of the femur 10 by the support member 16 and fixing means 17. The femur head holder 12 also includes a shaft 19 having an upper end to which the spherical femur head 11 is fixedly mounted. The shaft 19 is rotatably mounted in the housing 18.

As the leg mounted with the artificial hip-joint moves, the housing 18 fixed to the femur 10 rotates relatively to the shaft 19.

The shaft 19 is journalled at its middle portion by a taper roller bearing 20 and at its lower end portion by needle bearings 21 so that it can support load applied to the femur head 11 fixed to its upper end while rotating smoothly within the housing 18. The taper roller bearing 20 is retained by a retainer 20' received in the upper, large-diameter portion 22 of the housing 18. The housing 18 also has a lower, small-diameter portion 25 and a step 23 formed between the large and small-diameter portions 22 and 25. The retainer 20' has a taper inner surface having the same taper shape as the taper outer bearing surface of the taper roller bearing 20. The inner diameter of the retainer 20' at the lower end of the retainer 20' is smaller than the outer diameter of the taper roller bearing 20 at the lower end of the taper roller bearing 20. Accordingly, the lower end of the taper roller bearing 20 does not come into contact with the step 23 disposed at the lower end of the large-diameter portion 22 of the housing 18. By such a construction, it is possible to reduce, as much as possible, the friction occurring when the taper roller bearing 20 rolls.

The housing 18 can rotate with respect to the shaft 19 while supporting axial and radial components of the load applied to the femur head 11 by the weight of the user, by virtue of the taper roller bearing 20. Accordingly, the femur 10 can perform its flexion and extension movements even when the femur head 11 does not rotate in the acetabulum cup 14.

A journal 24 is mounted on the lower portion of the shaft 19 in order to minimize the friction generated when the needle bearings 21 roll. Journals 26 are also disposed between the needle bearings 21 and the inner surface of the smaller-diameter portion 25 of the housing 18 in order to minimize the friction generated when the housing 18 and shaft 19 rotate relatively to each other. In the illustrated case, another journal 26 is disposed around the shaft 19 between the taper roller bearing 20 and upper needle bearing 21.

Although two needle bearings 21 are disposed on the lower portion of the shaft 19 in the illustrated case, a single bearing may be employed in accordance with the kind and size of bearing used.

A stopper 28 is mounted to the lower end of the shaft 19 so as to prevent the needle bearings 21 and journals 24 and 26 from separating from the shaft 19.

The needle bearings 21 are proper to conduct functions of supporting the axial component of the load applied to the shaft 19 and reducing the friction generated during the rotation of the housing 18 with respect to the shaft 19 in a narrow space defined in the smaller-diameter portion 25 of the housing 18. Of course, such functions may be obtained using other well-known bearings, for example, journal bearings.

Once the shaft 19 is mounted in position in the housing 18, lubricant fills the interior of the housing 18. Thereafter, a magnetic fluid member 27 is mounted on the upper end of the larger-diameter portion 22 of the housing 18 to seal the opening defined between the upper end of the larger-diameter portion 22 and the shaft 19 extending therethrough. The lubricant serves to reduce the friction generated during the rotation of the shaft 19. Accordingly, formation of fine metal grains is reduced. O-rings 34 are fitted between the magnetic fluid member 27 and shaft 19 in order to prevent fine metal grains formed in the housing 18 from leaking between the magnetic fluid member 27 and shaft 19. In particular, the magnetic fluid member 27 has a magnet 30 and a magnetic fluid 32 so that it can be close in contact with the housing by virtue of the magnetic force of the magnet 30. Accordingly, although fine metal grains may be formed during the rotation of the bearings 20 and 21, they are surely confined in the interior of the housing 18. Therefore, it is possible to avoid osteolysis of the user due to fine metal grains.

The shaft 19 is also provided with an annular protrusion 29 at its upper portion in order to prevent the taper roller bearing 20 from separating from the shaft 19.

In the artificial hip-joint with the above-mentioned construction according to the present invention, the housing 18 rotates with respect to the shaft 19 while reducing the friction generated during its rotation by the taper roller bearing 20 and needle bearings 21. Since the housing 18 rotates with respect to the shaft 19, the user can perform flexion and extension movements of his hip even though the femur head 11 does not rotate in the acetabulum cup 14. In particular, since the generated friction is the rolling friction of the bearings, it is smaller than the face friction generated when the femur head 11 rotates in the acetabulum-cup 14. Accordingly, the artificial hip-joint of the present invention provides a superior effect as compared to the conventional artificial hip-joint.

Figure 4A:
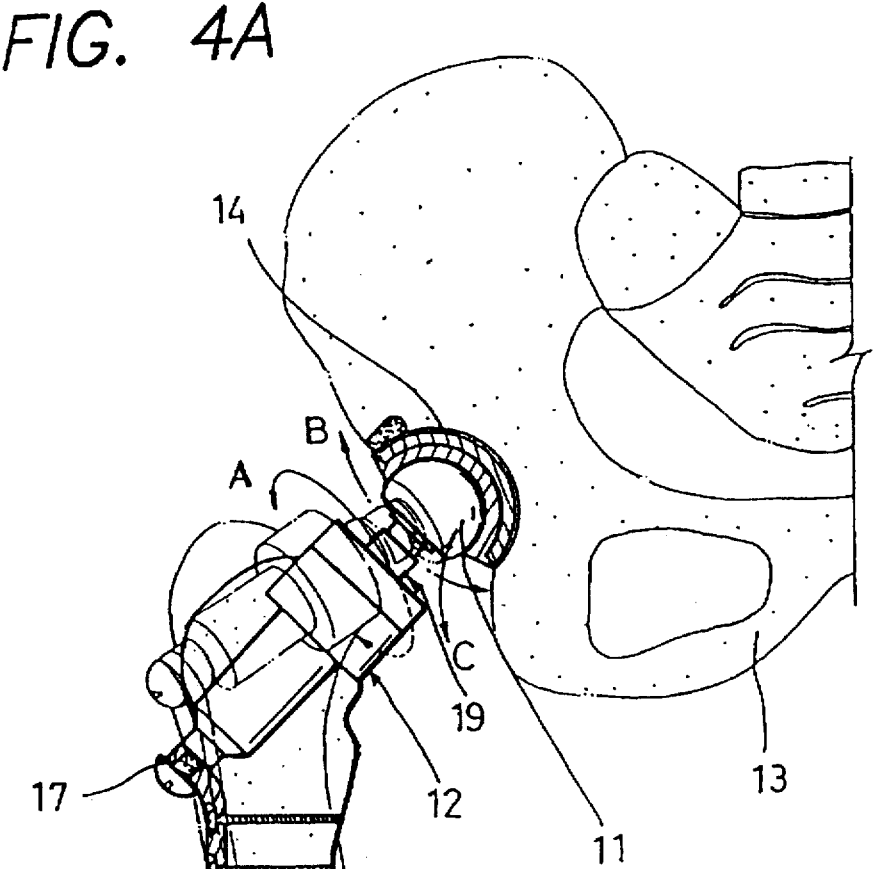
FIG. 4A is a view illustrating the operation of the artificial hip-joint shown in FIG. 2 when the user moves.
Figure 4B:
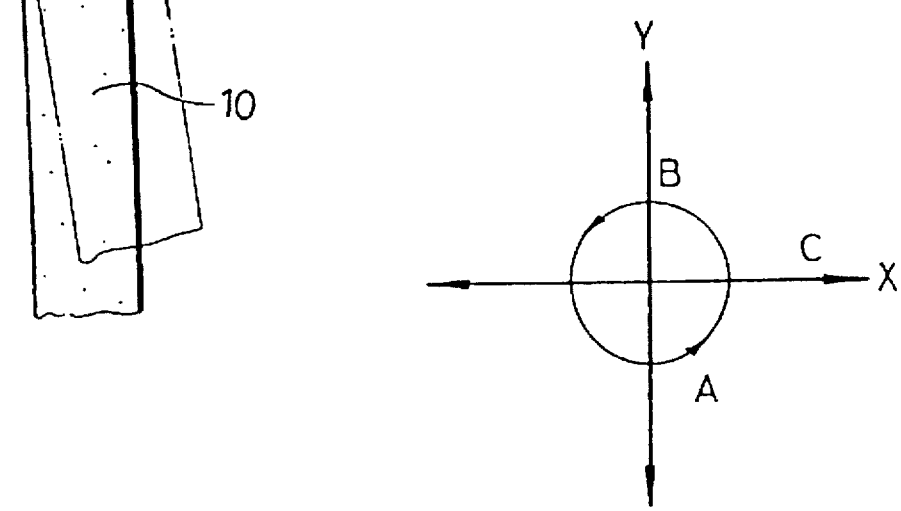
FIG. 4B is a view illustrating movements of the femur head conducted in the acetabulum cup.

When the user moves his hip to flexion or extension, internal rotation or external rotation, adduction and abduction, the femur head of his hip-joint pivots in the acetabulum cup. In other words, the femur head compositely performs an axial movement X or Y and a rotation A, as shown in FIG. 4B. In particular, the rotation A of the femur head, which is best shown in FIG. 4A, is most frequently conducted in user's everyday life, especially, when the user walks, goes upstairs or downstairs, or pedals a bicycle. Where the artificial hip-joint of the present invention is used, the relative rotation between its housing 18 and shaft 19 is not conducted when the femur head 11 moves along the X or Y-axis. However, the relative rotation between the housing 18 and shaft 19 is conducted when the rotation A of the femur head is required. In this case, the femur head 11 does not rotate because the housing 18 rotates with respect to the shaft 19. Accordingly, the pivotal movement of the femur head 11 is minimized. Therefore, it is possible to reduce the abrasion of the polyethylene layer occurring due to the friction between the outer surface of the femur head 11 made of metal and the inner surface of the polyethylene layer. This results in an improvement in the durability of the artificial hip-joint and an extension in the life of the hip-joint. Furthermore, it is possible to minimize occurrence of osteolysis caused by fine polyethylene particles formed upon the abrasion of the polyethylene layer. Consequently, it is possible to relieve the pain of the user and to reduce the hospital expense.

Figure 5:
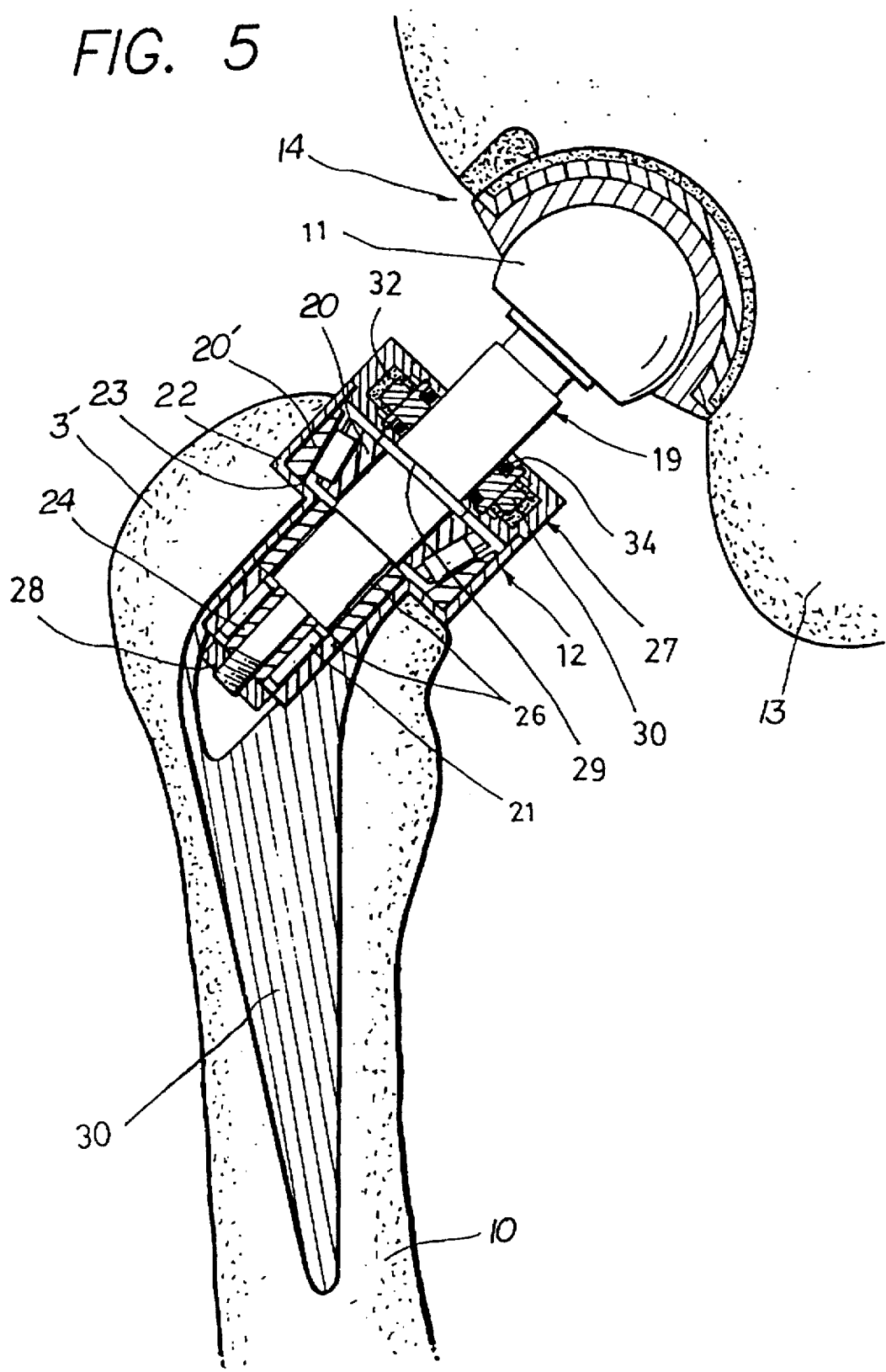
FIG. 5 is a sectional view illustrating an artificial hip-joint according to another embodiment of the present invention.

On the other hand, FIG. 5 is a sectional view illustrating an artificial hip-joint in accordance with another embodiment of the present invention in which its femur head holder 12 includes a stem 30 employed to support the shaft 19. The stem 30 is inserted at its lower end into a space formed in the central portion of the femur 3 after removing the marrow existing in that portion of the femur. In accordance with this embodiment, the stem 30 has an upper end embedded in the greater trochanter 3' of the femur 10. The upper end of the stem 30 has a hollow construction to support the shaft 19 in such a manner that the shaft 19 can rotate in the hollow construction. That is, the upper end of the stem 30 has the same construction as the upper portion of the housing 18 in the embodiment of FIG. 2.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. An artificial hip-joint comprising an artificial acetabulum cup implanted in the acetabulum of a user's pelvic bone, the artificial acetabulum cup consisting of a hollow hemispherical member made of a metal and a polyethylene layer formed on the inner surface of the hemispherical member, and a femur head holder fixed to a femur, the femur head holder comprising a spherical metal femur head pivotally held in the artificial acetabulum cup, wherein the femur head holder further comprises:

a shaft coupled at an upper end thereof to the femur head and adapted to support the femur head;

a housing extending inclinedly through the greater trochanter of the femur and adapted to receive the shaft therein in such a manner that it rotates with respect to the shaft; and bearing means mounted between the shaft and the housing and adapted to support axial and radial load applied to the shaft at the femur head by the weight of the user, the bearing means allowing the housing to rotate with respect to the shaft when the user performs a movement involving a rotation of the femur head in the acetabulum cup, so that the movement of the user can be conducted while preventing the rotation of the femur head in the acetabulum cup.

2. The artificial hip-joint in accordance with claim 1, wherein the bearing means comprises a taper roller bearing fitting around a middle portion of the shaft, and at least one needle bearing fitting around a lower portion of the shaft, whereby it can perform constructively stable rotating and load-supporting functions in a limited anatomical space given in the body of the user.

3. The artificial hip-joint in accordance with claim 2, wherein the housing has a larger-diameter portion provided at an upper portion thereof and adapted to receive the taper roller bearing, the larger-diameter portion having an opening at an upper end thereof, and a magnetic fluid member fixedly mounted to the upper end of the larger-diameter portion and adapted to seal the interior of the housing, the magnetic fluid member having an opening through which the shaft extends.

4. The artificial hip-joint in accordance with claim 3, wherein the sealed interior of the housing is filled with a lubricant for reducing a friction of the bearings.

5. The artificial hip-joint in accordance with claim 3, wherein the shaft is provided at an upper portion thereof with an annular protrusion adapted to prevent the taper roller bearing from separating from the shaft.

6. The artificial hip-joint in accordance with claim 1, wherein the housing has a lower end embedded in the femur and a stem provided at the lower end in such a manner that it is integral with the lower end, the stem being inserted into a space formed in a central portion of the femur after removing the marrow existing in the central portion of the femur.

7. The artificial hip-joint in accordance with claim 2, wherein the housing has a lower end embedded in the femur and a stem provided at the lower end in such a manner that it is integral with the lower end, the stem being inserted into a space formed in a central portion of the femur after removing the marrow existing in the central portion of the femur.

8. The artificial hip-joint in accordance with claim 3, wherein the housing has a lower end embedded in the femur and a stem provided at the lower end in such a manner that it is integral with the lower end, the stem being inserted into a space formed in a central portion of the femur after removing the marrow existing in the central portion of the femur.

9. The artificial hip-joint in accordance with claim 4, wherein the housing has a lower end embedded in the femur and a stem provided at the lower end in such a manner that it is integral with the lower end, the stem being inserted into a space formed in a central portion of the femur after removing the marrow existing in the central portion of the femur.

10. The artificial hip-joint in accordance with claim 5, wherein the housing has a lower end embedded in the femur and a stem provided at the lower end in such a manner that it is integral with the lower end, the stem being inserted into a space formed in a central portion of the femur after removing the marrow existing in the central portion of the femur.

* * * * *